(12) United States Patent
Leonardi et al.

(10) Patent No.: US 10,604,479 B2
(45) Date of Patent: Mar. 31, 2020

(54) CONTINUOUS PROCESS FOR THE ONE-POT SYNTHESIS OF METAL SALTS AND METAL COMPLEXES

(71) Applicants: VOLARE & CONNECTING, LLC, St. Louis, MO (US); Giuliano Leonardi, Isola Dovarese (IT)

(72) Inventors: Giuliano Leonardi, Isola Dovarese (IT); Giovanni Gasperoni, Isola Dovarese (IT)

(73) Assignee: NOVUS INTERNATIONAL, INC., St. Charles, MO (US)

( * ) Notice: Subject to any disclaimer, the term of this patent is extended or adjusted under 35 U.S.C. 154(b) by 673 days.

(21) Appl. No.: 15/037,433

(22) PCT Filed: Nov. 18, 2013

(86) PCT No.: PCT/IB2013/060216
§ 371 (c)(1),
(2) Date: May 18, 2016

(87) PCT Pub. No.: WO2015/071709
PCT Pub. Date: May 21, 2015

(65) Prior Publication Data
US 2016/0289180 A1  Oct. 6, 2016

(51) Int. Cl.
*C07C 319/20* (2006.01)
*A23K 40/20* (2016.01)
*A23K 40/25* (2016.01)
*A23K 20/20* (2016.01)
*C07C 51/41* (2006.01)

(52) U.S. Cl.
CPC ............ *C07C 319/20* (2013.01); *A23K 20/20* (2016.05); *A23K 40/20* (2016.05); *A23K 40/25* (2016.05); *C07C 51/412* (2013.01); *C07C 51/418* (2013.01)

(58) Field of Classification Search
CPC ........ A23K 40/20; A23K 40/25; A23K 20/20; C07C 51/418; C07C 51/412; C07C 319/20; C07C 59/50; C07C 53/00; C07C 57/00
See application file for complete search history.

(56) References Cited

U.S. PATENT DOCUMENTS

| 5,041,233 A * | 8/1991 | Kutny ................ C07C 51/412 510/152 |
| 2013/0172617 A1 | 7/2013 | Le Thiesse et al. |
| 2014/0356640 A1* | 12/2014 | Bastioli ................ C09D 103/02 428/535 |

FOREIGN PATENT DOCUMENTS

WO   WO-2012168891 A1 *  12/2012 ............. A01N 59/16

* cited by examiner

*Primary Examiner* — Subbalakshmi Prakash
(74) *Attorney, Agent, or Firm* — King & Schickli, PLLC

(57) ABSTRACT

A continuous process is described for the one-pot synthesis of compounds, such as metal salts and metal complexes, as well as optionally for the protection of the compounds thus obtained by coating and/or impregnation with suitable compounds.

19 Claims, 5 Drawing Sheets

CONTINUOUS PROCESS FOR THE ONE-POT SYNTHESIS OF METAL SALTS AND METAL COMPLEXES

RELATED APPLICATIONS

This application is a U.S. National Stage entry of International Patent Application PCT/IB2013/060216.

FIELD OF THE INVENTION

The present invention relates to a continuous process for the one-pot synthesis of compounds, such as metal salts and metal complexes, as well as optionally for the protection of the compounds thus obtained by coating and/or impregnation with suitable compounds.

STATE OF THE ART

One of the problems linked to salification reactions of liquid organic acids such as methionine hydroxy analogue, but also lactic acid or butyric acid, is the management of the phase transition of the reaction mixture. The reaction mixture evolves more or less quickly from a fluid consistency to a pasty, semi-solid state, then through a gradual hardening, until a very solid phase is observed which loses plasticity, becoming a solid subjected to mechanical breakage due to the progressive friability also associated with the drying of the product.

The management of such a viscometric profile in a discontinuous batch plant involves the need of using extremely rugged reactors with oversized mixing forces applied, such as to ensure the break up of the hardening mass in order to avoid the forming of monoblocks. Also, friable granules are obtained by drying, for example, the Ca-HMTBa salt to up to 1-2% humidity. The particle size distribution is therefore very broad and also includes particulate matter below 40 micrometers. The finer fraction is particularly troublesome and hardly manageable during the handling of the product. Traditional production systems, and in particular the batch system, generate an extremely wide Gaussian particle size distribution, i.e. a product having a disadvantageously heterogeneous appearance, which involves, in the subsequent use in the feeding industry of the Ca-HMTBa salt, a number of problems of homogeneity and miscibility.

The object of the present invention is to improve the production of metal salts and metal complexes, overcoming the drawbacks listed above.

SUMMARY OF THE INVENTION

The above object has been achieved by a continuous procedure for the one-pot synthesis of compounds as described in claim 1.

In another aspect, the present invention relates to compounds which can be obtained by said process.

The characteristics and the advantages of the present invention will become apparent from the following detailed description and from the working examples provided for illustrative purposes and from the accompanying Figures, wherein.

DETAILED DESCRIPTION OF THE INVENTION

Figure 1:
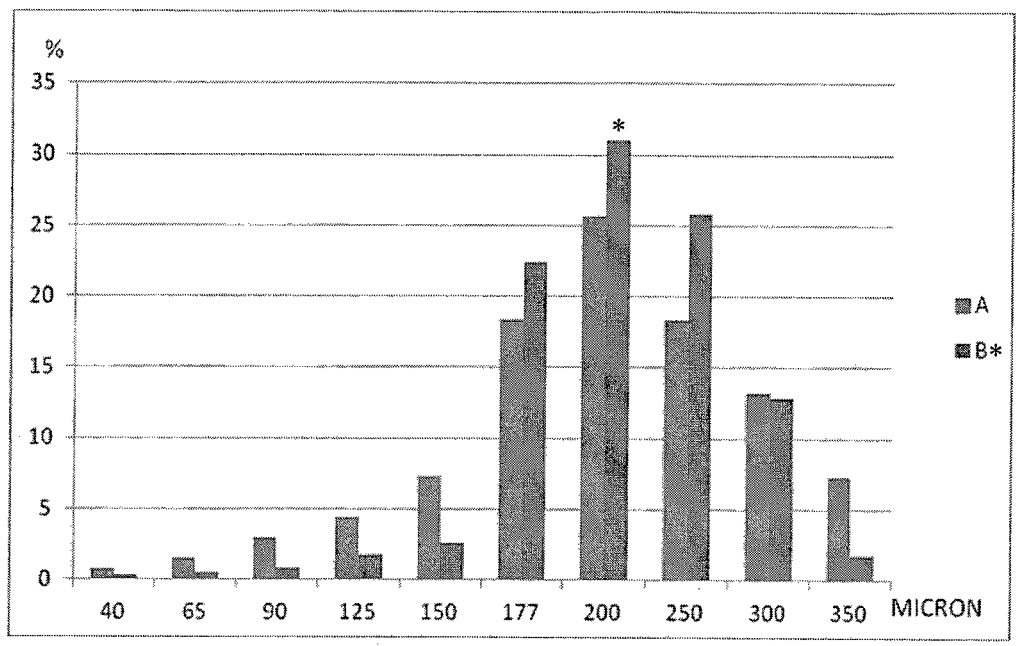
FIG. 1 shows the particle size profile of a compound obtained according to the process of the present invention.

The subject of the invention therefore is a continuous process for the one-pot synthesis of metal salts or metal complexes, comprising the steps of:

i) providing at least one tubular reactor provided with a cylindrical stator having at least one inlet and at least one outlet, at least one rotor coaxial to the stator provided with centrifugation and stirring means, and at least a first thermal jacket extended over at least 30% of the stator surface;

ii) setting said first thermal jacket to a temperature of 80-400° C.;

iii) setting a tangential speed of rotation of the rotor to 10-50 m/s;

iv) continuously feeding reagents for the synthesis of metal salts or metal complexes inletting the stator;

v) collecting the metal salts or metal complexes outletting the stator, wherein said reagents are:

at least one metal oxide, a metal hydroxide, a metal carbonate or a mixture thereof, at least one acid selected from methionine hydroxy analogue, lactic acid, formic acid, acetic acid, propionic acid, butyric acid, citric acid, malic acid, fumaric acid, oxalic acid, salicylic acid, benzoic acid, or at least one complexing agent selected from glycine, lysine, methionine, glutamic acid, ascorbic acid, a C6-C15 aromatic acid, a C6-C15 heteroaromatic acid, nicotinic acid, nicotinamide, rosmarinic acid, sulfanilic acid, or a mixture thereof.

In fact it has surprisingly been found that said process allows the drawbacks of the prior art to be overcome, at the same time advantageously increasing the yield; indeed, in terms of production efficiency, it is more tons per hour, thus reducing production costs and also reducing unpleasant odours that are inevitably released in batch plants. Furthermore, for the same amount of final product, compared to batch processes, the proCess of the present invention allows the use of small plants and significantly reduced powers, with clear advantages in terms of energy saving and dedicated industrial spaces.

The at least one tubular reactor includes a cylindrical stator provided with at least one thermal jacket, wherein there is at least one cylindrical rotor coaxial to the stator capable of rotating at high speed. The rotor is provided with centrifugation and stirring means, in particular blades, preferably adjustable blades.

With the term 'tangential speed' is meant the speed resulting at the end of the blades, i.e. at the point thereof closest to the inner wall of the stator.

Since the tangential speed of the rotor is very high, the fed reagents as well as the products that form along the stator, are actually thrown and held against the inner wall of the stator to form a thin layer of a few millimetres, typically 3-5 mm, which the rotating blades scrape so as to move forward reagents and products axially along the stator itself, at an advancing speed that also depends on how the blades are oriented. The formation of a thin layer has the main advantage of offering a wide surface of contact with the inner wall of the stator which, at the thermal jacket, exchanges heat thus promoting the synthesis of the final products. Another important advantage of the thin layer is the easiness with which gases and vapours can leave the reagents' mass, thus ensuring excellent drying efficiency and the possibility to use carbonates of metal salts instead of oxides as the carbon dioxide that is released does not give problems of foam formation.

The reagents fed therein, both solids and liquids, therefore substantially undergo two combined and synergistic actions by the rotor:
- the centrifugal force that throws and holds them against the inner wall of the stator, and
- the mixing effect by the centrifugation and stirring means, preferably blades, with which the rotor is provided, which continually remove them and push them forward in dynamic and turbulent thin layers along the wall of the stator, thereby promoting the synthesis of the final products by both thermal and mechanical actions.

Due to the very high centrifugal force, it follows that the orientation of the stator does not affect either the process conditions or the synthesis of the final products. Therefore, although a horizontal stator is preferred for construction practicality, a stator inclined with respect to the support ground may also be used.

In some embodiments, said at least one tubular reactor includes at least two rotors coaxial to the stator, arranged in series. In this way, it is possible to set at least two different tangential speeds, so that inside the stator there are areas with different turbulences. This advantageously allows the final particle size as well as the drying speed of the products to be varied according to the production needs. In particular, the first rotor can be operated so as to pre-mix the reagents, while the synthesis is completed at the second one. Moreover, it is also possible that at different rotors there are corresponding thermal jackets set to different temperatures.

Preferably, said at least one metal oxide, hydroxide or carbonate is at least one oxide, hydroxide or carbonate of Li, Na, K, Mg, Ca, Al, Mn, Fe, Cu, Zn, Co, Ni, Mo, Si, or Se.

Preferably, said at least one acid or said at least one complexing agent is salicylic acid, thiosalicylic acid, ascorbic acid, alanine, phenylalanine, glycine, isoleucine, leucine, methionine, proline, valine, tryptophan, tyrosine, glutamic acid, glycolic acid, lactic acid, malic acid, tartaric acid, propionic acid, butyric acid, citric acid, mandelic acid, methionine hydroxy analogue, sinapilic alcohol, cumarilic alcohol, coniferyl alcohol, sinapilic acid, cumarilic acid, coniferyl acid, cinnamic acid, ferulic acid, benzoic acid, benzenesulfonic acid, acid, naphthalene sulfonic acid, dipicolinic acid, phenylacetic acid, 1-naphthaleneacetic acid, nicotinic acid, nicotinamide, rosmarinic acid, sulfanilic acid or a mixture thereof.

Preferably, said metal salts or metal complexes are propionate, butyrate, citrate, benzoate, salicylate, maleate, fumarate, glycolate, lactate, lactate-gluconate, gluconate, glutamate, formiate, or methionine hydroxy analogue, of Li, Na, K, Mg, Ca, Al, Mn, Fe, Cu, or Zn.

According to preferred embodiments, said metal salts or metal complexes are methionine hydroxy analogue salt of Ca, Zn, Cu, Mn or Fe; butyrate of Na, Ca or Mg; propionate of Na, K, Mg, Ca, Zn, Cu, Mn, or Fe; Ca lactate; Ca lactate-gluconate; Fe fumarate or Ca formiate.

If said complexing agents or acids are not liquids at room temperature, the same are fed in the form of aqueous solutions, also oversaturated. Therefore, with the term 'liquid reagent' is meant both liquid complexing agents and acids at room temperature, and aqueous solutions thereof, when they are not liquids per se.

Reagents are then introduced at an inlet of the at least one reactor and the feeding of the reagents is ensured by the rapid rotation of the inner rotor and by the shape and orientation of the blades with which it is provided. As a result of such a rapid rotation of the rotor, the reagents are arranged in a thin layer on the inner wall of the stator. The high turbulence achieves a highly effective mixing of the reagents such as to ensure a progression of the salification reaction within a few seconds from the entrance into the reactor, with residence time even lower than 40 seconds.

The advancing speed of the materials inside of the stator, between the inlet of the reagents and the outlet of the final products, is a parameter that depends on the process conditions mentioned above, as well as on the construction features of the tubular reactor itself, but it preferably is in the range between 0.03 and 1 m/s, more preferably between 0.05 and 0.20 m/s.

The at least one reactor is also provided with at least a first outer thermal jacket, in which diathermic fluid circulates to provide the calories needed both to accelerate the synthesis kinetics, and to dry the final product. Since the materials are arranged in a thin layer on the inner wall of the stator, the heat exchange efficiency is very high and such as to ensure quick drying with excellent energy efficiency.

As said, one of the problems linked to salification reactions of liquid organic acids such as methionine hydroxy analogue, lactic acid or butyric acid, is the management of the phase transition of the reaction mixture to solid product. The reaction mixture evolves more or less quickly from a fluid consistency to a pasty, semi-solid state, then through a gradual hardening, until a very solid phase is observed which loses plasticity, becoming a solid subjected to mechanical breakage due to the progressive friability also associated with the drying of the product. The management of such a viscometric profile in a discontinuous batch plant involves the need of using extremely rugged reactors with oversized mixing forces applied, such as to ensure the break up of the hardening mass in order to avoid the forming of monoblocks.

The process of invention therefore surprisingly and advantageously overcomes such a problem, since the at least one tubular reactor can perfectly handle different viscosities, both because the amount of product in a continuous reactor is extremely small, and because the high turbulence does not allow the formation of a monobloc masses.

In such a condition, the salification reaction is quickly completed and the heat yielded by the wall ensures as much quick drying.

The evaporation efficiency is ensured above all by the heat exchange in a thin layer. The vapour formed can be easily removed by a small volume airflow that passes through the tubular reactor (in co-current or counter-current with the product). Since such a flow is confined inside the reactor, it is easily manageable in a closed circuit and allows the leakage of any solvents and/or volatile by-products to be restrained. In fact, as having to treat a very small air volume compared to those generated with traditional discontinuous systems, and easy to be captured, it is easily possible to use high-efficiency methods which applied to large volumes would be economically unsustainable (e.g. post-combustion). The reduced air volume further ensures excellent energy efficiency in the vapour recondensation phases.

Preferably, therefore, an airflow in a direction equal or opposite to the inlet-outlet direction of the stator flows inside the stator in order to remove any solvents and/or volatile by-products.

Friable granules are obtained by drying a metal salt to up to 1-2% humidity. The particle size distribution is therefore very broad and also includes particulate matter below 40 micrometers. The finer fraction is particularly troublesome and hardly manageable during the handling of the final product. Traditional production systems, and in particular the batch system, generate an extremely wide Gaussian particle size distribution, i.e. a product having a disadvantageously heterogeneous appearance, which involves, in the subsequent use in the feeding industry, a number of problems of homogeneity and miscibility.

The continuous process proposed instead has several advantages in terms of particle size control. In fact, the particle size curve which is obtained from the continuous process with a tubular reactor with coaxial bladed rotor has an extremely narrow profile compared to a batch process, i.e. the particle distribution is much more uniform.

Preferably, the metal salts or metal complexes collected in step v) are in the form of beads, pellets, multi-particulate, micronized particulate, agglomerates, micro-granules or granules. In a preferred embodiment, the tubular reactor is further provided with at least a second thermal jacket so that said two thermal jackets surround at least 70% of the stator surface.

Preferably, said second thermal jacket is arranged downstream of said first thermal jacket with respect to the inlet-outlet direction of the stator.

Preferably, the stator is provided with a second inlet.

More preferably, said second inlet is positioned between said thermal jackets.

Figure 2:
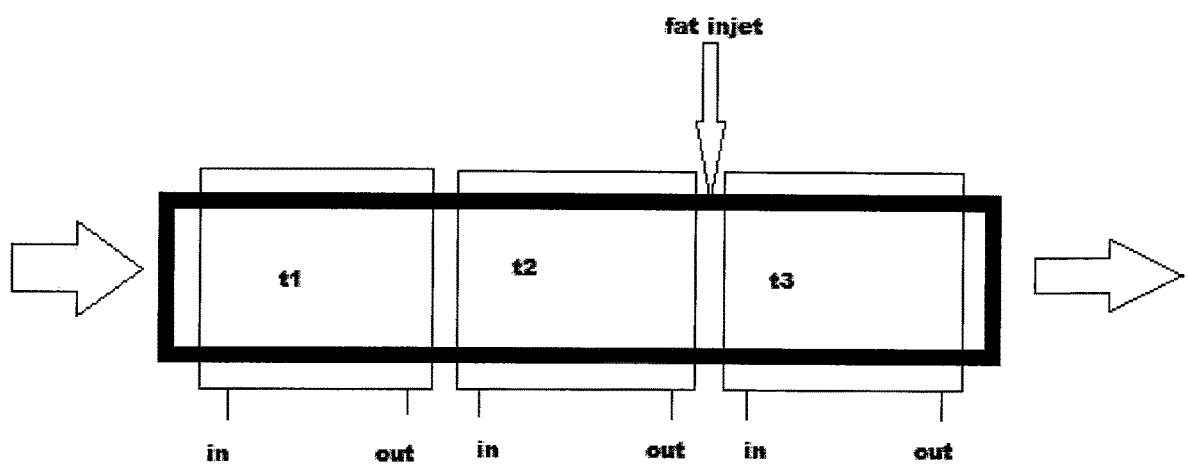
FIG. 2 shows a schematic longitudinal cross section view of a tubular reactor in a preferred embodiment of the invention.

In a particularly preferred embodiment, the tubular reactor has three thermal jackets that surround around at least 90% of the stator surface. With reference to FIG. 2, each thermal jacket can provide an equal or differentiated heating, i.e. t1, t2, and t3.

With the process of the invention, it is possible to further improve the particle size profile, i.e. to reduce the percentage of finer particles, by injecting a small percentage of liquid reagent, an acid or a complexing agent, in the last tract of the reactor through said second input. In this way, without increasing the overall humidity of the final product, through the injection of 0.1-5% by weight, preferably 0.2-0.5% by weight of liquid reagent on the total weight of the liquid reagent fed, the agglomeration of the finest particles is induced by modifying the particle size curve. In the practice, in the final part of the tubular reactor, through a suitable nozzle, a liquid reagent is injected which undergoes only a partial drying after it has had an aggregating function, owing to the high mixing turbulence. Therefore, the process of the invention may further comprise a step iv-a) of continuously feeding an additional amount of at least one acid or at least one complexing agent in liquid form, through said second input along the reactor.

By way of example, FIG. 1 shows the difference between the production of Ca-HMTBa according to the process of the invention ('A') and the production of Ca-HMTBa according to the process of the invention wherein 0.3% by weight of HMTBa is injected in the final part of the tubular reactor ('B').

The advantages are clear not only on the quality of the final product and in the later processing and use steps but also, in the last drying step, reducing the dust, which would otherwise be dragged by the flow of drying air, with clear reduction of the final yield and higher management costs, also due to the need for filtration of the output gases to reduce the environmental impact.

In order to further optimize the process, it is advantageously possible to eliminate the finer fraction by recirculating it to the reactor head. This allows the considerable advantages of avoiding sifting, separation and recovery of the non conforming (too fine or too large) fractions in output from the reactor, or at least the drastic reduction of the amount of such fractions, and the increase of the overall yield of the synthesis.

According to another preferred embodiment, the continuous process of the invention allows, always in one-pot, the resulting compounds to be protected by coating and/or impregnation with suitable compounds. This has multiple purposes, including:
  protection from oxidation,
  protection of certain compounds from rumen or gastric digestion,
  reduction of volatility, aggression or unpleasant odour, and
  improvement of the particle size smoothness and uniformity.

The use of a tubular reactor with bladed coaxial rotor at a high speed of rotation, by means of appropriate adjustments, allows said protection to be implemented with a great effectiveness, at the same time in an exceptionally simple and practical manner.

Therefore, the process of the invention can further comprise the step iv-b) of continuously feeding through said second inlet a lipid matrix for coating and/or impregnating the metal salts or metal complexes.

In fact, said second input may allow the feeding of a small percentage of liquid reagent in order to further improve the particle size profile, i.e. to reduce the percentage of finer particles, as described above, or it may be used for feeding said lipid matrix. Not only the effect of reducing the finest particles, but especially of impregnating/coating the final products is obtained in this second case.

Preferably, said lipid matrix is rapeseed oil, soybean oil, seed oil, olive oil, wheat germ oil, palm oil, coconut oil, sesame oil, peanut oil, cottonseed oil, olein, C3-C36 fatty acid, C3-C36 mono, di- or triglyceride fatty acid, animal, vegetable, mineral oil or synthetic wax, spermaceti, lanolin, paraffin, hydrogenated fats or oils, tea tree oil (melaleuca oil), or a drying oil such as linseed oil, walnut oil, poppy oil, or a mixture thereof.

C3-C36 fatty acids comprise saturated fatty acids, monounsaturated fatty acids and polyunsaturated fatty acids such as propanoic acid, butanoic acid, pentanoic acid, esanoic acid, eptanoic acid, octanoic acid, nonanoic acid, decanoic acid, undecanoic acid, dodecanoic acid, tridecanoic acid, tetradecanoic acid, pentadecanoic acid, hexadecanoic acid, heptadecanoic acid, octadecanoic acid, nonadecanoic acid, eicosanoic acid, docosanoic acid, tetracosanoic acid, hexacosanoic acid, octacosanoic acid, triacontanoic acid, dotriacontanoic acid, cis-7-hexadecenoic acid, cis-9-octadecenoic acid, trans-9-octadecenoic acid, cis-11-octadecenoic acid, cis-9-eicosenoic acid, cis-11-docosenoic acid, cis-13-docosenoic acid, cis-15-tetracosenoic acid, 9,12-octadecadienoic acid, 9,11-octadecadienoic acid, 9,12,15-octadecatrienoic acid, 6,9,12,15-octadecatetraenoic acid, 5,8,11,14-eicosatetraenoic acid, 5,8,11,14,17-eicosapentaenoic acid, 7,10,13,16,19-docosapentaenoic acid and 4,7,10,13,16,19-docosaesaenoic acid.

Preferably, said second jacket is a cooling jacket, in order to discharge the finished product at a temperature lower than that of the hot reaction and drying steps, as well as in particular at a temperature lower than the solidification point of the lipid matrix used.

In the drawing of FIG. 2, for example, temperatures t1 and t2 are suitable for conducting the drying reaction; t3, on the other hand, is arranged to cool the product in order to bring it to a temperature more suitable for the subsequent manipulation. Exploiting this situation, it is possible to introduce an amount of suitable protective compound in the liquid state on the still hot product, which impregnates and/or coats the granules, thus making them waterproof, owing to the progressive cooling along the longitudinal line of the reactor. In this way, products having optimal particle size and consistency are obtained.

Preferably, said second thermal jacket is set at a temperature of 10-30° C., corresponding to t3 in FIG. 2.

Alternatively, the process of the invention may further comprise the step iv-c) of continuously feeding through said second inlet a polymeric solution for coating and/or impregnating the metal salts or metal complexes.

By 'polymer solution' it is meant an aqueous solution, also colloidal, comprising at least one synthetic or natural polymer. Said polymer may be oligosaccharide, cellulose acetate phthalate, cellulose acetate succinate, hydroxypropyl methylcellulose phthalate, hydroxypropyl methylcellulose acetate succinate, polyvinyl acetate phthalate, hydroxyethylcellulose phthalate, cellulose acetate tetrahydro phthalate, copolymers of methacrylate-methacrylic acid, sodium alginate, stearic acid, starch, guar gum, xanthan gum, or a mixture thereof.

Preferably, said polymers are rumen or gastro-resistant polymers.

In this alternative, by the action of the heating/drying by the at least one thermal jacket, the aqueous solvent of the polymeric solution evaporates, so that the polymer impregnates or coats the final products.

In this case, preferably, said second jacket is a jacket providing further heating, in order to facilitate the evaporation of the aqueous solvent.

In some preferred embodiments, the input mass flow rate of said lipid matrix or said polymer is up to 50% by weight of the final metal salts or metal complexes, more preferably up to 20% by weight.

As will be seen from the following Examples, for instance, calcium salt of methionine hydroxy analogue (in short, 'Ca-HMTBa') was obtained, of which 90-60% Ca-HMTBa and 10-40% of the lipid matrix, with excellent additional advantages compared to the non impregnated/coated salt: a larger particle size, more suitable for ruminants, a product having a much less intense sulphide smell, and especially a rumen resistance which has grown from 40% typical of the Ca-HMTBa salt up to 60-80% depending on the lipid proportion and on the type of lipid matrix used.

With the term 'rumen-protected product', it is meant a dietary supplement (vitamin, amino acid, or organic acid) protected from chemical and biological attacks that typically occur in the first part of the digestive system of ruminants. With the process of the invention, the impregnation/coating with lipid matrix or polymer ensures a high stability of the rumen-protection during the industrial processing. In fact, the nutritional principles are immersed in the lipid matrix or in the polymer, not merely coated with a thin film, so that the partial melting, deformation or breakage of the mass do not impair the protective effect. The impregnation/coating ensures excellent stability of the rumen-protection even after the mechanical actions due both to the feed formulation processing and during chewing: even in case of breakage and deformation, the mass may be only minimally affected.

The choice of the lipid matrix, as well as of the polymers according to the invention ensures an excellent resistance to rumen degradation. In fact, such a lipid matrix is not digestible by the rumen microflora because there are no lipases in the rumen, thereby ensuring excellent by-pass levels. In the intestine then, the lipid matrix is completely digested due to the effect of pancreatic lipases and the protected additive is released and then normally absorbed.

With the term 'by-pass fraction', it is meant the part of additive (expressed as percentage of the total used) that does not undergo degradation due to the residence in a rumen for a predetermined time. There are several methods to determine such a resistance, also in laboratory. In the simplest version, the protected additive is placed in a solution at predetermined pH and T and then, after removing by filtration the fraction not passed in the solution, the solubilised part is determined (considering the same susceptible of rumen bacterial degradation) and after that, by difference, what has not passed in the solution is defined as by-pass fraction.

A further advantage of the process of the invention is the possibility to use carbonates, in particular calcium carbonate ($CaCO_3$) in place of CaO lime, as reagents.

In traditional salification processes, the use of a carbonate has always been problematic in that, once placed to react in a traditional batch mixer, it releases carbon dioxide resulting in the formation of foams and thereby, in an increase in volume, as well as in major problems of mass management.

In the continuous process of the invention, instead, the reagent mass is distributed in a thin layer on the inner wall of the stator, due to the strong turbulence (and thus high mixing among the reagents). This ensures an increase in reactivity so as to allow the use of carbonates in an effective manner (in the continuous process, the reaction time is mostly of a few seconds) because the carbon dioxide that is released, easily and quickly leaves the thin reaction layer (a few mm) without giving any problem of foams.

The advantages of such a solution are both economic and practical. Carbonates cost significantly less than the corresponding oxides, such as lime (CaO). Moreover, even from the point of view of workability and handling, the differences are even more remarkable. Lime, in particular, is corrosive to materials and organic tissues; calcium carbonate is harmless; lime is extremely hygroscopic and degrades over time by absorbing carbon dioxide from the air, while calcium carbonate is inert.

More in general, therefore, the process of the invention advantageously allows to treat also reagents that may develop gaseous substances advantageously without any problem and without having to modify the reactor.

Optionally, the metal salts or metal complexes in output from the tubular reactor are separated from air, and possibly by the fine particulate, by using instruments such as a cyclone.

In another aspect, the present invention relates to metal salts or metal complexes impregnated and/or coated with at least one lipid matrix or at least one polymer, obtainable by the continuous process as described above.

Preferably, these are compositions consisting of 50-90% metal salts or metal complexes, 10-50% lipid matrix, the balance being water.

Alternatively, these are compositions consisting of 60-95% metal salts or metal complexes, 40-5% polymer, the balance being water.

More preferably, the compositions are in the form of granules consisting of 65-72% metal salt or metal complex, 34-27% lipid matrix or polymer, the balance being water.

In preferred embodiments, said compositions have less than 3% water.

It should be understood that all aspects identified as preferred and advantageous for the continuous process are to be deemed as similarly preferred and advantageous also for the metal salts or metal complexes impregnated and/or coated with at least one lipid matrix or at least one polymer of the present invention.

In another aspect, the present invention relates to the use of metal salts or metal complexes impregnated and/or coated with at least one organic matrix or at least one polymer of the invention as food additive in the livestock field. In fact, the metal salts or metal complexes, suitably stored and carried by the lipid matrix or by the polymer, can be used for the above uses, while overcoming the drawbacks associated thereto in the prior art.

Below are working examples of the present invention provided for illustrative purposes.

EXAMPLES

Example 1

Production of Ca-HMTBa According to the Process of the Invention

A tubular reactor was used, having a bladed coaxial rotor, at a high speed of rotation, having the following technical features:
inner diameter of the cylinder 250 mm;
length of the reactor 1500 mm;
evaporating surface approximately 1.2 $m^2$.

The reactor was provided with a jacket in which diathermic oil at a temperature of 120° C. circulates. The reagents used were:
Lime (CaO) Molecular Weight=56.08
Methionine hydroxy analogue (MW=150) (Rhodimet AT88®, in which 88% HMTBa and 12% water).

The reagents were conditioned at room temperature of 25° C. The two reagents were continuously fed to the tubular reactor head by a weight metering device and a volumetric metering device, respectively.

The mass flow rates of the two reagents were set as follows:
HMTBa 3 kg/min (corresponding to 180 kg/hour)
CaO 560 g/min (corresponding to 33.6 Kg/hour)
Tangential speed of rotation of the rotor of 30 m/s.
Estimated time of residence in the reactor: 15-20 seconds.
Input temperature 25° C.
Temperature measured at the outlet, at the cyclone discharge, 65° C.

The Ca-HMTBa salt was obtained, having measured humidity 1% and a content in HMTBa of 87.5%.

Example 2

Production of Ca-HMTBa According to the Process of the Invention, by Using Calcium Carbonate as a Calcium Source A tubular reactor was used, having a bladed coaxial rotor, at a high speed of rotation, having the following technical features:
inner diameter of the cylinder 250 mm;
length of the reactor 1500 mm;
evaporating surface approximately 1.2 $m^2$.

The reactor was provided with a jacket in which diathermic oil at a temperature of 130° C. circulates. The reagents used were:
Fine ground calcium carbonate from sedimentary limestone rocks ($CaCO_3$) Molecular Weight=100.08
Methionine hydroxy analogue (MW=150) (Rhodimet AT88®, in which 88% HMTBa and 12% water).

The reagents were conditioned at room temperature of 25° C. The two reagents were continuously fed to the tubular reactor head by a weight metering device and a volumetric metering device, respectively.

The mass flow rates of the two reagents were set as follows:
HMTBa 2.5 kg/min (corresponding to 150 kg/hour)
$CaCO_3$ 730 g/min (corresponding to 43.8 Kg/hour)
Tangential speed of rotation of the rotor of 30 m/s.
Estimated time of residence in the reactor: 25-30 seconds.
Input temperature 25° C.
Temperature measured at the outlet, at the cyclone discharge, 60° C.

The Ca-HMTBa salt was obtained, having measured humidity 0.5% and a content in HMTBa of 87.7%.

Example 3

Production of Ca-HMTBa According to the Process of the Invention, Including Impregnation and Coating with Lipid Matrix A tubular reactor was used, having a bladed coaxial rotor, at a high speed of rotation, having the following technical features:
inner diameter of the cylinder 250 mm;
length of the reactor 1500 mm;
evaporating surface approximately 1.2 $m^2$.

Figure 3:
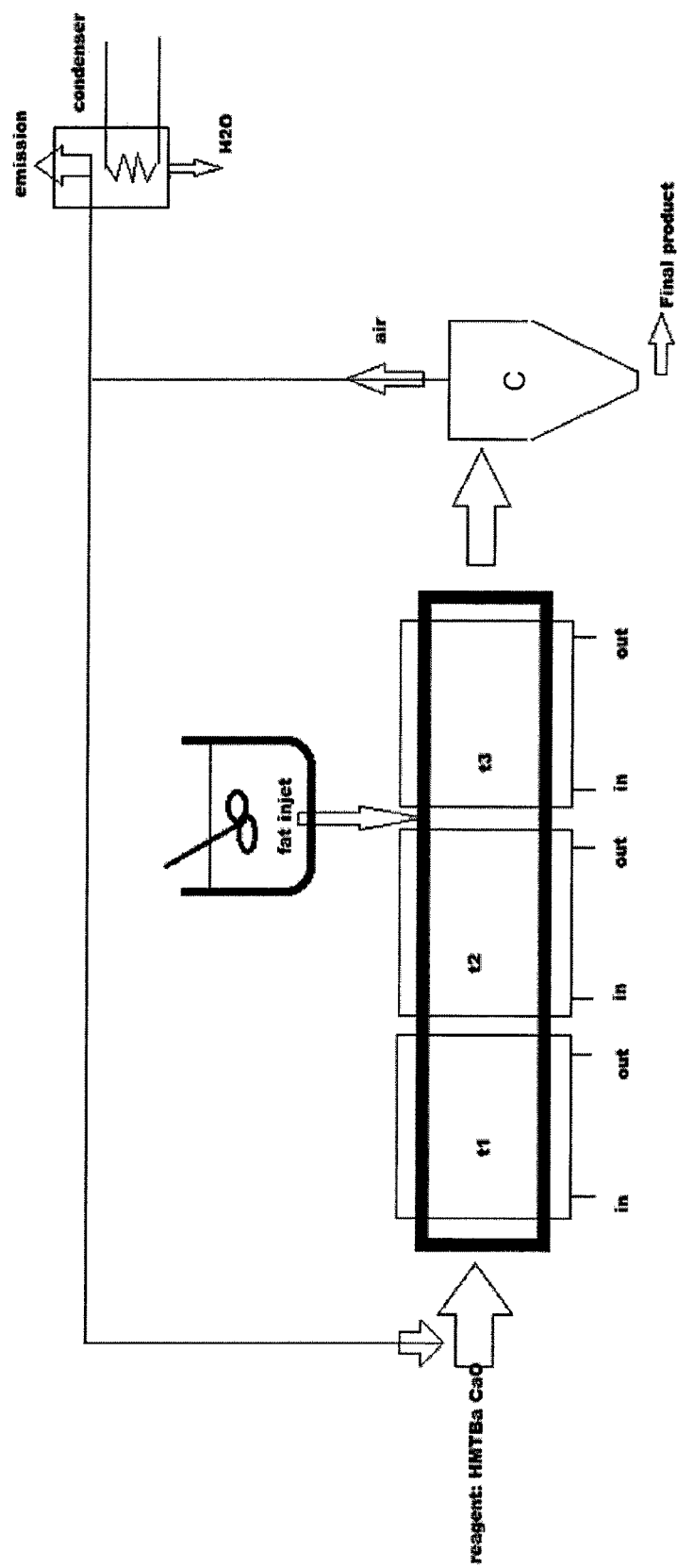
FIG. 3 shows a schematic longitudinal cross section view of a tubular reactor in another preferred embodiment of the invention.

As schematically shown in FIG. 3, the reactor was provided with three independent jackets for heat exchange: diathermic oil was circulated in the first two at a temperature of 120° C. (t1=t2); water was circulated in the third one at a temperature of 15° C. (t3). The reagents used were:
Lime (CaO) Molecular Weight=56.08
Methionine hydroxy analogue (MW=150) (Rhodimet AT88®, in which 88% HMTBa and 12% water)
as lipid matrix: vegetable stearin; mp 65-67° C.

The reagents were conditioned at room temperature of 25° C. The two reagents were continuously fed to the tubular reactor head by a weight metering device and a volumetric metering device, respectively.

The mass flow rates of the first two reagents were set as follows:
HMTBa 3 kg/min (corresponding to 180 kg/hour)
CaO 560 g/min (corresponding to 33.6 Kg/hour)
Tangential speed of rotation of the rotor of 30 m/s.
Estimated time of residence in the reactor: 15-20 seconds.
Input temperature 25° C.

Vegetable stearin in the molten state, i.e. kept at 85° C. under constant mixing, was introduced through a special nozzle placed between the second and the third jacket ('fat inject' in FIG. 3). The stearin flow rate was set to about 600 g/min (about 36 Kg/hour).

In this point of the reactor, i.e. at the nozzle, the Ca-HBTBa salt formed has a temperature of about 80-85° C.

From this point onwards the salt, impregnated with molten stearin, undergoes a rapid cooling by the third jacket, which in addition to solidifying the stearin, induces an agglomeration of the finer salt particulate.

The temperature measured at the outlet, at the cyclone discharge, was 65° C.

The Ca-HMTBa salt was obtained, having measured humidity 1% and a content in HMTBa of 70%, having also a vegetable stearin content of 17%. The product thus obtained had a granular appearance, the fine particulate was absent.

Once placed in water, it proved to be essentially insoluble, confirming that the lipid matrix, in addition to having impregnated the salt, had also externally coated it, thus isolating it from the outside.

Example 4

Production of Zn-HMTBa According to the Process of the Invention

A tubular reactor was used, having a bladed coaxial rotor, at a high speed of rotation, having the following technical features:
inner diameter of the cylinder 250 mm;
length of the reactor 1500 mm;
evaporating surface approximately 1.2 m$^2$.
The reagents used were:
White zinc oxide (ZnO) Molecular Weight=81.37; titre in zinc 78-80%
Methionine hydroxy analogue (MW=150) (Rhodimet AT88®, in which 88% HMTBa and 12% water).
The reagents were conditioned at room temperature of 25° C. The two reagents were continuously fed to the tubular reactor head by a weight metering device and a volumetric metering device, respectively.

The reactor was provided with a jacket in which diathermic oil at a temperature of 120° C. circulates. The mass flow rates of the two reagents were set as follows:
HMTBa 2 kg/minute (corresponding to 120 kg/hour)
ZnO 480 g/minute (corresponding to 29 Kg/hour)
Tangential speed of rotation of the rotor of 35 m/s.
Estimated time of residence of the reactor: 20-25 seconds
Input temperature: 25° C.
Temperature measured at the outlet, at the cyclone discharge, 60° C.

The Zn-HMTBa salt was obtained, having measured humidity <1%, content in HMTBa 81.2% and 17.7% zinc.

Figure 4A:
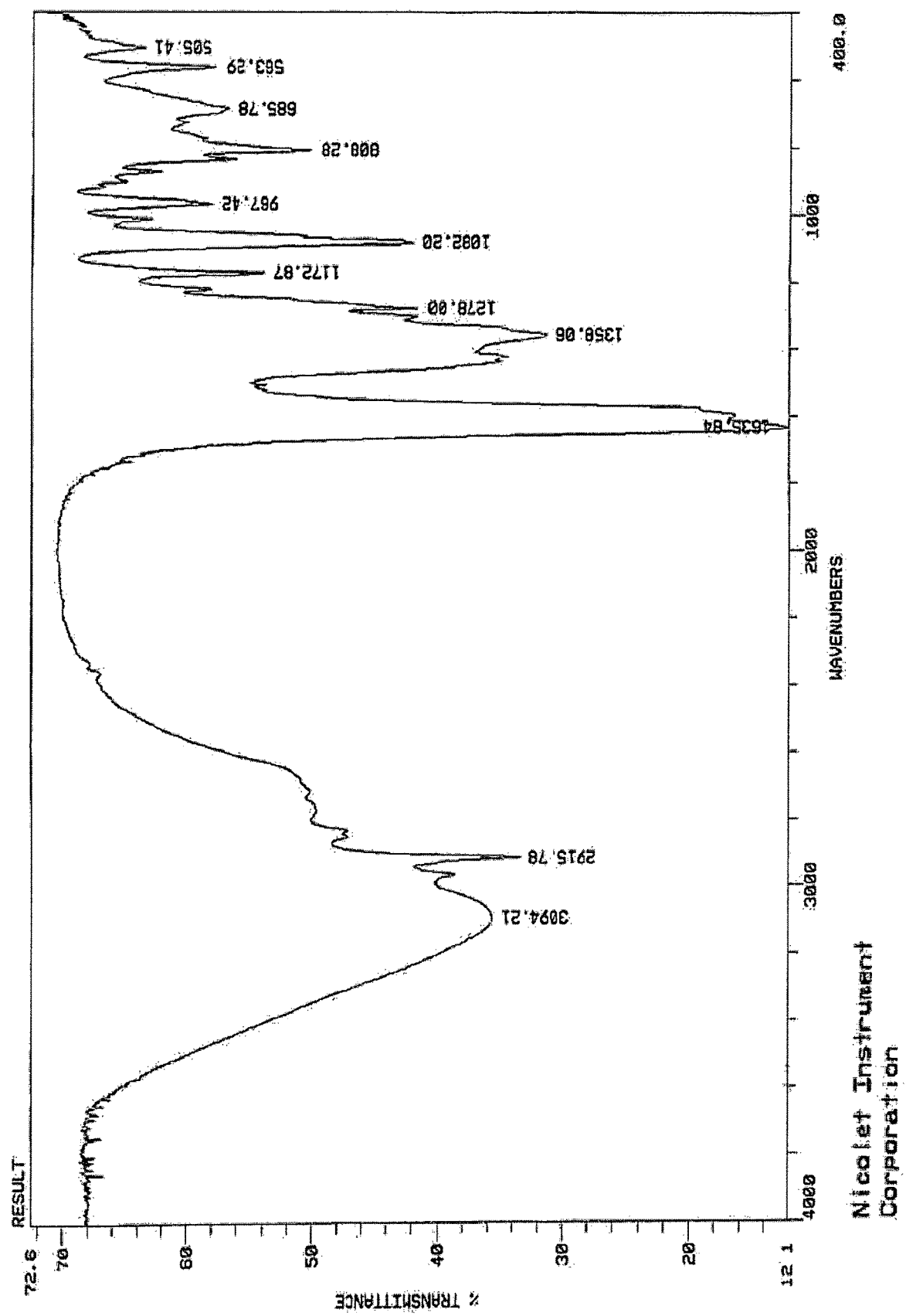
FIG. 4 shows the FT-IR spectrum recorded in absorption between 4000 and 400 cm$^{-1}$ of Zn-HMTBa (a) and HMTBa (b), as per Example 4.
Figure 4B:
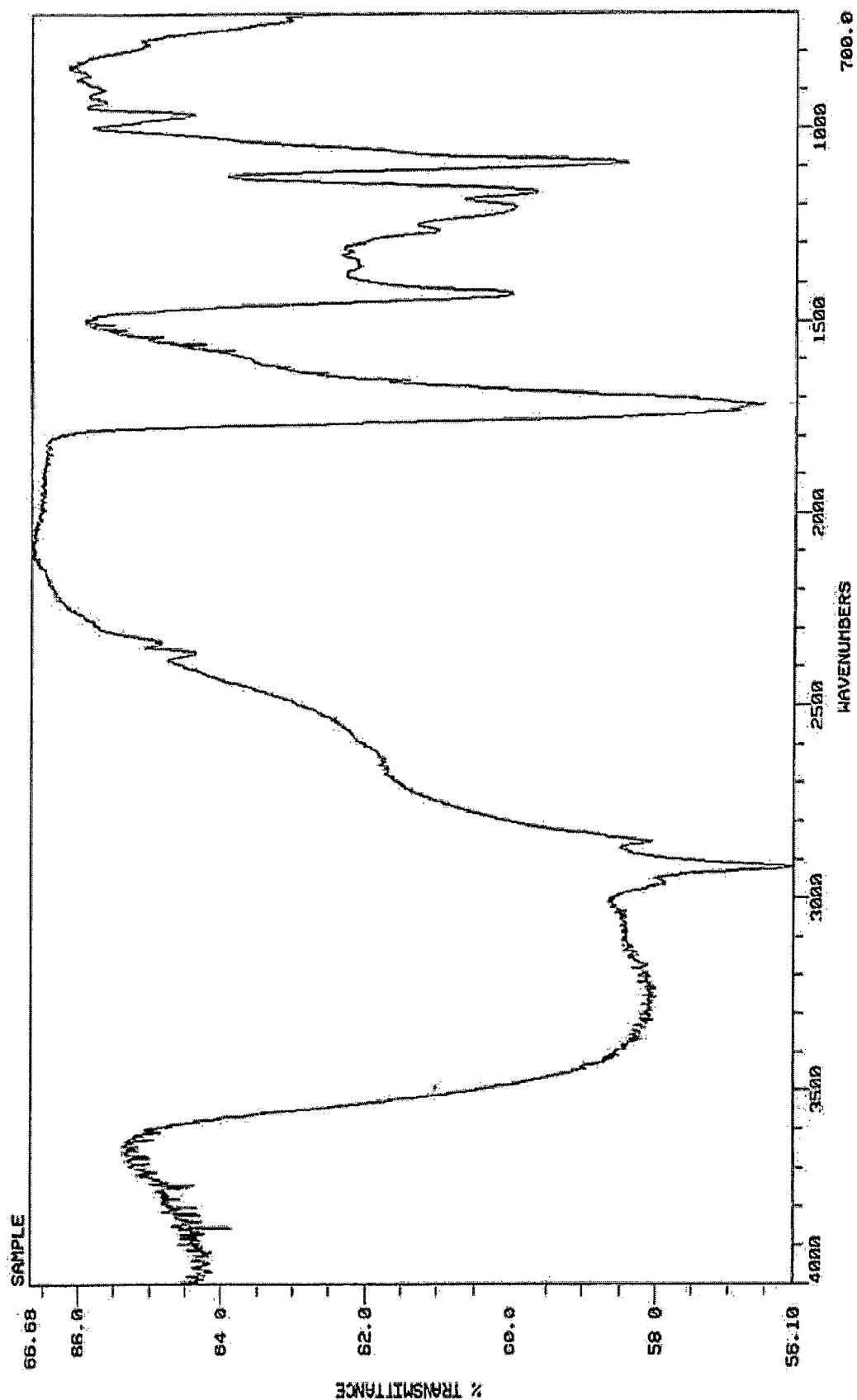

FIG. 4a shows the FTIR spectrum of the Zn-HMTBa salt, while FIG. 4b shows that of the starting reagent HMTBa. The spectrum in FIG. 4a shows several characteristic bands among which that due to the asymmetric stretching of the carboxyl group at 1635 cm$^{-1}$.

The position of such a band is significantly shifted to lower frequencies compared with the free hydroxy acid (1720 cm$^{-1}$) spectrum in FIG. 4b, as is expected due to the deprotonation and chelation of the metal ion.

Figure 5:
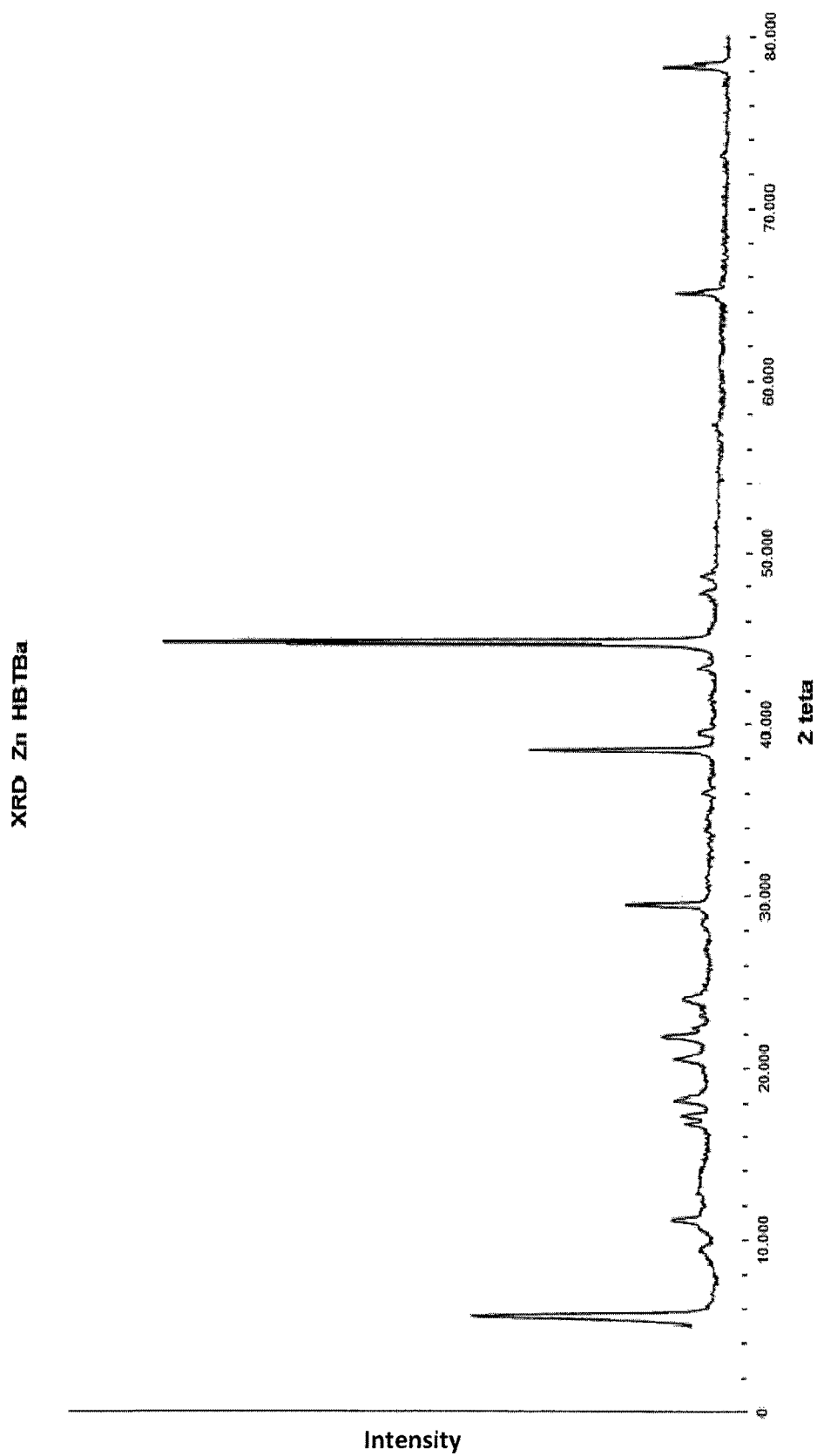
FIG. 5 shows the XRD spectrum of Zn-HMTBa, as per Example 4.

FIG. 5 shows the XRD spectrum of the Zn-HMTBa salt. [Philips Analytical X-Ray Goniometer: θ-θ scan with coverage angle 0-160° in 2θ. Source: CuKα and CuKβ]. The X-ray diffraction investigation has revealed that the Zn-HMTBa salt obtained from the process is crystalline. In fact, the diffraction spectrum shows several characteristic peaks.

Example 5

Production of Cu-HMTBa According to the Process of the Invention, Including Impregnation and Coating with Lipid Matrix The copper compounds are often responsible for inducing oxidation due to labile additives, such as vitamins, in premixes and animal feed. The copper compounds also have interesting functions, not only of a nutritional nature but also of bacterial control at the intestinal level. The use of a lipid coating on copper compounds can on the one hand reduce the chemical aggressiveness in the feed, on the other can release the compounds only when the intestinal lumen is reached and lipases are contacted thus disrupting the lipid matrix. In order to achieve such an object with an extremely advantageous system both from the production and economic point of view, a pilot production of HMTBa-chelated copper and then at the same time an impregnation with a high melting, low iodine number stearin was conducted (the 'iodine number' indicates the degree of unsaturation of an oil/fat; the low iodine number means that there are no double bonds and, therefore, that all fats are saturated with the dual effect of having a high melting point and not being susceptible to oxidative rancidity at the double bond (easily induced by copper)). A tubular reactor was used for such a test, with coaxial finned rotor, at a high speed of rotation of pilot size, as in Example 4. The reactor was provided with three independent jackets for heat exchange: diathermic oil was circulated in the first two at a temperature of 120° C.; water was circulated in the third one at a temperature of 15° C.

The reagents used were:
Copper hydroxide (64% Cu) (Cu (OH)$_2$) Molecular Weight=97.5
Methionine hydroxy analogue (MW=150) (Rhodimet AT88®, in which 88% HMTBa and 12% water).
lipid matrix: vegetable stearin, mp 65–67° C.
The reagents were conditioned at room temperature of 25° C. The two reagents were continuously fed to the tubular reactor head by a weight metering device and a volumetric metering device, respectively.

The mass flow rates of the two reagents were set as follows:
HMTBa 2 kg/minute (corresponding to 120 kg/hour)
Cu(OH)$_2$ 580 g/minute (corresponding to 34.8 Kg/hour)
Tangential speed of rotation of the rotor of 35 m/s.
Input temperature 25° C.

Vegetable stearin in molten state (kept at 85° C. under constant mixing) was introduced through a special nozzle placed between the second and the third jacket.

In this point, the estimated temperature of the Cu(HBTBa)$_2$ salt was 70–75° C.

Stearin flow rate about 380 g per minute (23 Kg/hour).

From this point onwards the product, impregnated with molten stearin, underwent a rapid cooling by the third jacket, which in addition to solidifying the stearin, induced an agglomeration of the finer particulate.

The estimated flow rate of finished product in output was about 150 Kg/hour.

Estimated time of residence of the reactor: 40-50 seconds.
Temperature measured at the outlet, at the cyclone discharge, 35° C.
Analytical contents measured:
Ether extract (fats) 15%
HMTBa 70%
Copper 13.1%
Humidity: <1%
Fine particles (below 40 μM)<1%

The advantages achieved by the process of the present invention are clear from the detailed description and from the examples above. In particular, this process proved to be surprisingly and advantageously quick and convenient, since it allows the one-pot synthesis of a ready-to-use product to be continuously obtained, optionally impregnating and/or coating it with a lipid matrix or a polymer that allows keeping it for a long time and maintaining a high activity and bioavailability over time.

The invention claimed is:
1. A continuous process for the one-pot synthesis of metal salts or metal complexes, comprising the steps of:
   i) providing at least one tubular reactor provided with a cylindrical stator having at least one inlet and at least one outlet, at least one rotor coaxial to the stator provided with centrifugation and stirring means, and at least a first thermal jacket, wherein the first thermal jacket extends over at least 30% of the stator surface;
   ii) setting said first thermal jacket to a temperature of 80-400° C.;
   iii) setting a tangential speed of rotation of the rotor to 10-50 m/s;
   iv) continuously feeding reagents for the synthesis of metal salts or metal complexes inletting the stator;
   v) collecting the metal salts or metal complexes outletting the stator,
wherein said reagents are:
   at least one metal oxide, a metal hydroxide, a metal carbonate or a mixture thereof,
   at least one acid selected from methionine hydroxy analogue, lactic acid, formic acid, acetic acid, propionic acid, butyric acid, citric acid, malic acid, fumaric acid, oxalic acid, salicylic acid, benzoic acid, or at least one complexing agent selected from glycine, lysine, methionine, glutamic acid, ascorbic acid, a C6-C15 aromatic acid, a C6-C15 heteroaromatic acid, nicotinic acid, nicotinamide, rosmarinic acid, sulfanilic acid, or a mixture thereof, wherein at least one of said at least one acid, said at least one complexing agent, or said mixture thereof is a liquid reagent, and wherein an airflow in a direction equal or opposite to the inlet-outlet direction of the stator flows inside the stator.

2. The process according to claim 1, wherein said at least one metal oxide, hydroxide or carbonate is at least one oxide, hydroxide or carbonate of Li, Na, K, Mg, Ca, Al, Mn, Fe, Cu, Zn, Co, Ni, Mo, Si, or Se.

3. The process according to claim 1, wherein said at least one acid or said at least one complexing agent is salicylic acid, thiosalicylic acid, ascorbic acid, alanine, phenylalanine, glycine, isoleucine, leucine, methionine, proline, valine, tryptophan, tyrosine, glutamic acid, glycolic acid, lactic acid, malic acid, tartaric acid, propionic acid, butyric acid, citric acid, mandelic acid, methionine hydroxy analogue, sinapilic alcohol, cumarilic alcohol, coniferyl alcohol, sinapilic acid, cumarilic acid, coniferyl acid, cinnamic acid, ferulic acid, benzoic acid, benzenesulfonic acid, acid, naphthalene sulfonic acid, dipicolinic acid, phenylacetic acid, 1-naphthaleneacetic acid, nicotinic acid, nicotinamide, rosmarinic acid, sulfanilic acid or a mixture thereof.

4. The process according to claim 1, wherein said metal salts or metal complexes are propionate, butyrate, citrate, benzoate, salicylate, maleate, fumarate, glycolate, lactate, lactate-gluconate, gluconate, glutamate, formiate, or methionine hydroxy analogue, of Li, Na, K, Mg, Ca, Al, Mn, Fe, Cu, or Zn.

5. The process according to claim 4, wherein said metal salts or metal complexes are methionine hydroxy analogue salt of Ca, Zn, Cu, Mn or Fe; butyrate of Na, Ca or Mg; propionate of Na, K, Mg, Ca, Zn, Cu, Mn, or Fe; Ca lactate; Ca lactate-gluconate; Fe fumarate or Ca formiate.

6. The process according to claim 1, wherein the centrifugation and stirring means are blades.

7. The process according to claim 1, wherein said tubular reactor is further provided with at least a second thermal jacket so that said two thermal jackets surround at least 70% of the stator surface.

8. The process according to claim 7, wherein said second thermal jacket is arranged downstream of said first thermal jacket with respect to the inlet-outlet direction of the tubular reactor.

9. The process according to claim 8, wherein the stator is provided with a second inlet.

10. The process according to claim 9, further comprising a step iv-a) of continuously feeding through said second inlet an additional amount of 0.1-5% by weight of the total weight of liquid reagent of at least one acid or at least one complexing agent in liquid form.

11. The process according to claim 9, further comprising a step iv-b) of continuously feeding through said second inlet a lipid matrix for coating and/or impregnating the metal salts or metal complexes.

12. The process according to claim 11, wherein said lipid matrix is rapeseed oil, soybean oil, seed oil, olive oil, wheat germ oil, palm oil, coconut oil, sesame oil, peanut oil, cottonseed oil, olein, C3-C36 fatty acid, C3-C36 mono, di- or triglyceride fatty acid, animal, vegetable, mineral oil or synthetic wax, spermaceti, lanolin, paraffin, hydrogenated fats or oils, tea tree oil (melaleuca oil), or a drying oil selected from linseed oil, walnut oil, poppy oil, or a mixture thereof.

13. The process according to claim 9, further comprising a step iv-c) of continuously feeding through said second inlet a polymeric solution for coating and/or impregnating the metal salts or metal complexes.

14. The process according to claim 13, wherein said polymeric solution includes at least one polymer selected from oligosaccharides, cellulose acetate phthalate, cellulose acetate succinate, hydroxypropyl methylcellulose phthalate, hydroxypropyl methylcellulose acetate succinate, polyvinyl acetate phthalate, hydroxyethycellulose phthalate, cellulose acetate tetrahydro phthalate, copolymers of methacrylate-methacrylic acid, sodium alginate, stearic acid, starch, guar gum, xanthan gum, or a mixture thereof.

15. A composition obtained by the process according to claim 11 or claim 13 consisting of 50-90% metal salt or metal complex, 10-50% lipid matrix, the balance being water; or consisting of 60-95% metal salt or metal complexes, 40-5% polymer, the balance being water.

16. The composition of claim 15, in the form of granules consisting of 65-72% metal salt or metal complex, 34-27% lipid matrix or polymer, the balance being water.

17. The composition according to claim 15, wherein said metal salt or metal complex is propionate, butyrate, citrate, benzoate, salicylate, maleate, fumarate, glycolate, lactate, lactate-gluconate, gluconate, glutamate, formiate, or methionine hydroxy analogue of Li, Na, K, Mg, Ca, Al, Mn, Fe, Cu, or Zn complexes are propionate, butyrate, citrate, benzoate, salicylate, maleate, fumarate, glycolate, lactate, lactate-gluconate, gluconate, glutamate, formiate, or methionine hydroxy analogue, of Li, Na, K, Mg, Ca, Al, Mn, Fe, Cu, or Zn.

18. The composition according to claim 17, wherein said metal salts or metal complexes are methionine hydroxy analogue salt of Ca, Zn, Cu, Mn or Fe; butyrate of Na, Ca or Mg; propionate of Na, K, Mg, Ca, Zn, Cu, Mn, or Fe; Ca lactate; Ca lactate-gluconate; Fe fumarate or Ca formiate.

19. The composition according to claim 18, wherein said metal salt is a methionine hydroxy analogue salt.

\* \* \* \* \*